United States Patent [19]

Yokoyama et al.

[11] Patent Number: 6,057,157
[45] Date of Patent: May 2, 2000

[54] FLOWER INITIATION INDUCER

[75] Inventors: Mineyuki Yokoyama, Yokohama; Atsushi Takimoto, Kyoto; Shinji Inomata, Yokohama; Kazuo Komatu, Yokohama; Seiichi Yoshida, Yokohama; Okihiko Sakamoto, Yokohama; Kiyotaka Kojima, Tokyo, all of Japan

[73] Assignee: Shiseido Company, Ltd., Tokyo, Japan

[21] Appl. No.: 08/945,554

[22] PCT Filed: Mar. 4, 1997

[86] PCT No.: PCT/JP97/00658

§ 371 Date: Nov. 4, 1997

§ 102(e) Date: Nov. 4, 1997

[87] PCT Pub. No.: WO97/32478

PCT Pub. Date: Sep. 12, 1997

[30] Foreign Application Priority Data

Mar. 4, 1996 [JP] Japan .................................. 8-073162

[51] Int. Cl.⁷ .................................................. A01B 79/00
[52] U.S. Cl. ........................... 435/430; 47/58.1; 504/189; 504/320
[58] Field of Search .............................. 435/430; 47/58.1; 504/189, 320

[56] References Cited

PUBLICATIONS

Dix et al. J. Biol. Chem. vol. 260(9). pp. 5351–5357, 1985.
Grechkin et al. European Journal of Biochem. vol. 199 (2). pp. 451–457, 1991.
A. Yamamoto et al., "Lipids", *Product Specificity of Rice Germ Lipoxygenase,* vol. 15, No. 1., pp. 1–5, (1979).
A Yamamoto et al., "Agric. Biol. Chem.", *Partial Purification and Study of Some Properties of Rice Germ Lipoxygenase,* 44 (2), pp. 443–445, (1980).
W.C. Song et al., "Science", *Purification of an Allene Oxide Synthase and Identification, of the Enzyme as a Cytochrome P–450,* vol. 253, pp. 781–784, (Aug. 16, 1991).
W.C. Song et al., "Proc. Natl. Acad. Sci. USA", *Molecular cloning of an allene oxide synthase: A cytochrome P450 specialized for the metabolism of fatty acid hydroperoxides,* vol. 90, pp. 8519–8523, (Sep. 1993).

*Primary Examiner*—Leon B. Lankford, Jr.
*Attorney, Agent, or Firm*—Foley & Lardner

[57] ABSTRACT

An agent for inducing flower bud formation in plants comprising an unsaturated fatty acid having an oxo group and a hydroxy group, a hydroperoxy group, or an oxo group, a hydroxy group, and a hydroperoxy group; a method for preparing said agent for inducing flower bud formation; and, a method for inducing flower bud formation using said agent for inducing flower bud formation are provided.

18 Claims, 4 Drawing Sheets

FLOWER INITIATION INDUCER

TECHNICAL FIELD

The present invention relates to agents for inducing flower bud formation, methods for the production thereof, and methods for inducing flower bud formation using said agents for inducing flower bud formation.

BACKGROUND ART

It is well known that flower formation of plants is controlled by day length. It has also been found that the part that responds to the day length is the leaf blade and flower formation begins at the meristem and that a certain signal is sent from the leaf blade via the petiole and the stem to the meristem where flower formation starts. The signal is called "florigen." It is obvious that the isolation and identification of florigen would enable the artificial control of the flowering timing of plants irrespective of day length, which would no doubt have enormous impacts on many plant-related fields.

Thus, attempts have been made to artificially control the timing of flowering of plants by elucidating the mechanism of the process of flower formation.

For example, it was found that gibberellin, a growth hormone of plants, when applied, causes flower bud formation of long-day plants even under short-day conditions and that pineapples start flower formation after the application of α-naphthalene, a synthetic auxin, which is currently used industrially.

However, it is also known that these plant hormones are florigen-related substances, which are different from florigen itself.

Therefore, it is often required to set various conditions such as the timing and the environments of applying these plant hormones to plants, etc. As a result, there is a need for further advancement of flowering methods, or more specifically, the establishment of flowering techniques through isolation and identification of substances which are directly involved in flower bud formation.

It has also been reported that the phenomenon of flower bud formation based on photoperiodis is inhibited by a dry stress in the plants of the genus Pharbitis, the genus Xanthium, and the genus Lolium (for the genus Pharbitis and the genus Xanthium: Aspinall 1967; for the genus Lolium: King and Evans). Furthermore, it has also been reported that flower bud formation is induced by low temperature (Bernier et al. 1981; Hirai et al. 1994), high illumination (Shinozaki 1972), poor nutrition (Hirai et al. 1993), or shortage of nitrogen sources (Wada and Totuka 1982; Tanaka 1986; Tanaka et al. 1991).

However, these reports are mere observations of phenomena and do not directly specify the above-mentioned florigen and there is still a need for the establishment of the flowering method based on the understanding from the material aspect.

DISCLOSURE OF THE INVENTION

Thus, the problem to be solved by the present invention is to locate an inducer of flower bud formation that is directly involved in flowering and thereby to provide an agent for inducing flower bud formation having said inducer of flower bud formation as an active ingredient.

The present invention first provides an agent for inducing flower bud formation comprising a fatty acid of 4 to 24 carbon atoms having an oxo group and a hydroxy group and containing 0 to 6 double bonds.

The present invention also provides an agent for inducing flower bud formation comprising a fatty acid of 4 to 24 carbon atoms having an oxo group, a hydroxy group and a hydroperoxy group and containing 0 to 6 double bonds.

The present invention further provides an agent for inducing flower bud formation comprising a fatty acid of 4 to 24 carbon atoms having a hydroperoxy group and containing 0 to 6 double bonds.

The present invention further provides an agent for inducing flower bud formation which is obtained by incubating a yeast mass or a tissue of an angiospermal plant or an aqueous extract thereof with a fatty acid.

The present invention further provides an agent for inducing flower bud formation comprising various agents for inducing flower bud formation mentioned above and norepinephrine.

The present invention further provides a kit for inducing flower bud formation comprising an agent for inducing flower bud formation.

The present invention further provides a method of inducing flower bud formation comprising applying said agent for inducing flower bud formation to a plant.

MODE FOR CARRYING OUT THE INVENTION

Fatty Acids Having the Activity of Inducing Flower Bud Formation

The first embodiment of the present invention of fatty acids having the activity of inducing flower bud formation is a fatty acid of 4 to 24 carbon atoms having an oxo group and a hydroxy group and containing 0 to 6 double bonds. Said oxo group and said hydroxy group preferably constitute an α-ketol structure or a γ-ketol structure:

$$\underset{(\alpha\text{-ketol})}{-\overset{O}{\overset{\|}{C}}-\overset{OH}{\overset{|}{C}H}-} \qquad \underset{(\gamma\text{-ketol})}{-\overset{O}{\overset{\|}{C}}-CH=CH-\overset{OH}{\overset{|}{C}}-}$$

The number of double bonds is preferably two to five, more preferably two or three, and most preferably two. The number of carbon atoms is preferably 14 to 22, more preferably 16 to 22, and most preferably 18. The representative fatty acids having the α-ketol structure include 9-hydroxy-10-oxo-12(Z),15(Z)-octadecadienoic acid (sometimes referred to herein as Factor-C (FC)) and 12-oxo- 13-hydroxy-9(Z),15(Z)-octadecadienoic acid:

9-hydroxy-10-oxo-12(z),15(Z)-octadecadienonic acid 12-oxo-13-hydroxy-9(z),15(Z)-octadecadienoic acid.

Also, the fatty acids having the γ-ketol structure include 10-oxo-13-hydroxy-11(E),15(Z)-octadecadienoic acid and 9-hydroxy-12-oxo-10(E),15(Z)-octadecadienoic acid:

10-oxo-13-hydroxy-11(E),15(Z)-octadecadienoic acid 9-hydroxy-12-oxo-10(E),15(Z)-octadecadienoic acid.

The second embodiment of the present invention of the fatty acids having the activity of inducing flower bud formation is a fatty acid of 4 to 24 carbon atoms having an oxo group, a hydroxy group, and a perhydroxy group (—O—OH) and containing 0 to 6 double bonds. Said oxo group and said hydroxy group constitute an α-ketol structure or a γ-ketol structure and most preferably an α-ketol structure. The number of double bonds is preferably two to five, more preferably two or three, and most preferably two. The number of carbon atoms is preferably 14 to 22, more preferably 16 to 22, and most preferably 18. The representative fatty acids belonging to this embodiment include 9-hydroperoxy-12-oxo-13-hydroxy-10(E),15(Z)-octadecadienoic acid and 9-hydroxy-10-oxo-13-hydroperoxy-11(E),15(Z)-octadecadienoic acid:

9-hydroperoxy-12-oxo-13-hydroxy-10(E),15(Z)-octadecadienoic acid 9-hydroxy-10-oxo-13-hydroperoxy-11(E),15(Z)-octadecadienoic acid.

The third embodiment of the present invention of the fatty acids having the activity of inducing flower bud formation is a fatty acid of 4 to 24 carbon atoms having a hydroperoxy group and containing 0 to 6 double bonds. Said oxo group and said hydroxy group constitute an α-ketol structure or a γ-ketol structure and most preferably an α-ketol structure. The number of double bonds is preferably two to five, more preferably two or three, and most preferably three. The number of carbon atoms is preferably 14 to 22, more preferably 16 to 22, and most preferably 18. The representative fatty acids belonging to this embodiment include 9-hydroperoxy-10(E),12(Z),15(Z)-octadecatrienoic acid and 13-hydroperoxy-9(Z),11(E),15(Z)-octadecatrienoic acid:

9-hydroperoxy-10(E),12(Z),15(Z)-octadecatrienoic acid 13-hydroperoxy-9(Z),11(E),15(Z)-octadecatrienoic acid.

Among the various fatty acids mentioned above, 9-hydroxy-10-oxo-12(Z),15(Z)-octadecadienoic acid, i.e. Factor C, may be prepared by the extraction methods from plants, chemical synthetic methods, and the enzymatic methods. Other fatty acids may be prepared by the chemical synthetic methods or the enzymatic methods.

The Extraction Methods

*Lemna paucicostata* used as a source material in this extraction method is a small water plant floating on the surface of a pond or a paddy field of which each thallus floating on the water produces one root in the water. Its flowers are formed on the side of the thallus in which two male flowers comprising only one stamen and a female flower comprising one pistil are enveloped in a small common bract.

This *Lemna paucicostata* has a relatively fast growth rate (i.e., the rate of flower formation is rapid. The *Lemna paucicostata* 151 strain used for checking induction of flower bud formation in the assay system mentioned below conducts flower formation within only seven days), and has excellent properties as an assay system related to flower bud formation such as the ability of controlling induction of flower bud formation, etc.

The ability of inducing flower bud formation has been at least found in the homogenates of this *Lemna paucicostata*.

Furthermore, the fraction obtained by removing the supernatant from the mixture of the supernatant and the precipitate that was obtained by subjecting said homogenate to centrifuge (8000×g, ca. 10 minutes) may be used as a fraction containing Factor C.

Thus, Factor C can be isolated and/or purified using the above-mentioned homogenate as the starting material.

As a starting material preferred in terms of preparation efficiency there may be mentioned an aqueous solution obtained after floating or immersing *Lemna paucicostata* in the water. The aqueous solution is not specifically limited so long as the *Lemna paucicostata* is viable.

The specific embodiments of the preparation of this aqueous solution will be described in the examples below.

The immersing time may be, but is not limited to, two to three hours at room temperature.

In preparing the starting material for Factor C by the method mentioned above, it is preferred to subject *Lemna paucicostata* to a specific stress in advance which enables induction of flower bud formation for better efficiency of Factor C production.

Specific examples include dry stress, heat stress, osmotic stress, etc. as the above-mentioned stress.

The dry stress may be imposed, for example, at a low humidity (preferably at a relative humidity of 50% or lower) at room temperature, preferably at 24 to 25° C. by leaving the *Lemna paucicostata* spread out on a dry filter paper. The drying time in this case is longer than about 20 seconds, preferably 5 minutes or more, and more preferably 15 minutes or more.

The heat stress may be imposed, for example by immersing *Lemna paucicostata* in a hot water. The temperature of the hot water in this case can be 40° C. to 65° C., preferably 45° C. to 60° C., and more preferably 50° C. to 55° C. As the time required for treating in the hot water, about five minutes is sufficient, but at a relatively low temperature, for example the treatment of *Lemna paucicostata* in a hot water of about 40° C., treatment for more than two hours is preferred. Furthermore, after said heat stress treatment, *Lemna paucicostata* is preferably returned to cold water as quickly as possible.

The osmotic stress may be imposed, for example, by exposing *Lemna paucicostata* to a solution of high osmotic pressure such as a solution of a high sugar concentration and the like. The sugar concentration in this case is 0.3M or higher for mannitol, for example, and preferably 0.5M or higher. The treatment time is one minute or longer in the case of a solution of 0.5M mannitol, and preferably three minutes or longer.

Thus, the starting material containing the desired Factor C may be obtained.

The strains of Lemna paucicostata that constitute a basis for the various starting materials mentioned above are preferably, but not limited to, the strains that especially efficiently produce an inducer of flower bud formation (for example, Lemna paucicostata strain 441). Such a strain of Lemna paucicostata can be obtained by the conventional selection methods or by the gene engineering methods.

Subsequently, the starting material thus prepared may be subjected to the following isolation and/of purification methods to produce the desired Factor C.

It is to be understood that the separation methods as described herein are only illustrative and that these separation methods do not limit in any way the separation methods of Factor C from the above-mentioned starting materials.

First the above-mentioned starting material is subjected to solvent extraction to extract a Factor C-containing component. The solvents used in such solvent extraction methods include, but not limited to, chloroform, ethyl acetate, ether, butanol, and the like. Among these solvents chloroform is preferred because it can remove impurities relatively easily.

By washing and/or concentrating the oil layer fractions obtained by this solvent extraction by a commonly known method and then by subjecting to high performance liquid chromatography using a column for the reverse-phase partition column chromatography such as an ODS (octadodecyl silane) column etc. to isolate and/of purify the fractions having the ability of inducing flower bud formation, Factor C can be isolated.

In addition, it is also possible to use combinations of other commonly known methods for separation such as ultra-filtration, gel filtration chromatography and the like.

Chemical Synthetic Methods

Next, chemical synthetic methods of fatty acids having the effect of inducing flower bud formation of the present invention will be explained.

Factor C (i.e., 9-hydroxy-10-oxo-12(Z),15(Z)-octadecadienoic acid) can be synthesized according to the following scheme (A) (Method 1).

Nonanedioic acid mono ethylester (I) used as the starting material is reacted with N,N'-carbonyldiimidazole to make an acid imidazolide, which is then reduced with LiAlH$_4$ at a low temperature to convert to the aldehyde (3). On the other hand, cis-2-hexen-1-ol (4) is reacted with triphenyl phosphine and carbon tetrabromide. The thus obtained (5) is reacted with triphenyl phosphine and then reacted in the presence of n-BuLi with chloroacetaldehyde to construct a cis olefin which is converted to (7). Then, after reaction with methylthio methyl p-tolyl sulfone, it is reacted in the presence of NaH with the previously derived aldehyde (3). The derived secondary alcohol (9) is protected with tert-butyldiphenylsilylchloride, acid-hydrolyzed, and deprotected to convert to Factor C (9-hydroxy-10-oxo-12(Z),15(Z)-octadecadienoic acid) (12).

Furthermore, as the second method for chemically synthesizing Factor C, there is mentioned a method in which 1,9-nonanediol (1') is used in place of nonanedionic acid mono ester (1) as the starting material, which is oxidized with $MnO_2$ to give a dialdehyde (2') which is further oxidized with $KMnO_4$ to give a monoaldehyde monocarboxylic acid (3') and then esterified to form an intermediate compound (3) in the above scheme (1). The subsequent reactions can be carried out according to the scheme (A) in the above method (1). The reaction route from 1,9-nonanediol (1') to the intermediate (3) is shown in scheme (B)

Also, 12-oxo-13-hydroxy-9(Z),15(Z)-octadecadienoic acid can be synthesized according to, for example, the synthetic scheme (C). That is, nonanedioic acid mono ethyl ester (1) as the starting material is reacted with thionyl chloride to give an acid chloride (2), which is then reduced with $NaBH_4$ to give an acid alcohol (3). Then, after the free carboxylic acid is protected, it is reacted with triphenyl phosphine and carbon tetrabromide and the thus obtained (5) is reacted with triphenyl phosphine and then further reacted in the presence of n-BuLi to give chloroacetaldehyde to construct a cis olefin which is converted to (6). Then, after reaction with methylthio methyl p-tolyl sulfone, it is reacted in the presence of nBuLi with the aldehyde (3) which was separately derived from the PCC oxidation of cis-2-hexen-1-ol (8), and finally deprotected to give 12-oxo-13-hydroxy-9(Z),15(Z)-octadecadienoic acid 1(10).

Furthermore, 10-oxo-13-hydroxy-11(E),15(Z)-octadecadienoic acid can be synthesized according to, for example, the synthetic scheme (D). That is, methyl vinyl ketone (1) used as the starting material is reacted with trimethylsilyl chloride in the presence of LDA and DME, and to the silyl ether (2) thus obtained MCPBA and trimethylamine hydrofluoric acid are added at a low temperature (-70° C.) to give a ketoalcohol (3). Then, after the carbonyl group is protected, triphenyl phosphine and trichloroacetone are used as the reaction reagents to give (5) without adding a chloride to the olefin. Then in the presence of tributylarsine and $K_2CO_3$, formic acid is reacted to construct a trans olefin to give a chloride (7). Then, (7) and the aldehyde (8) obtained by the PCC oxidation of cis-2-hexen-1-ol are reacted to give (9). Furthermore, a binding reaction of (9) and 6-heptenoic acid (10) is conducted and finally deprotected to give 10-oxo-13-hydroxy-11(E),15(Z)-octadecadienoic acid (11).

The Enzymatic Method

Next, the methods of enzymatic synthesis are explained. For example, Factor C of the present invention may be synthesized by the enzymatic method in the following manner. As the starting material for the enzymatic synthesis of Factor C, α-linolenic acid may be used. α-linolenic acid is an unsaturated fatty acid contained in plants and the like in a relative abundance. An α-linolenic acid that was isolated and/or purified using the commonly known methods from these animals and plants etc. may be used as the starting material for production of Factor C, or it is also possible to use commercial products.

In this enzymatic method, α-linolenic acid as the substrate is brought to the action of lipoxygenase (LOX) to introduce a hydroperoxy group (—OOH) at position 9. Lipoxygenase is an oxidoreductase that introduces molecular oxygen as a hydroperoxy group into an unsaturated fatty acid having the cis,cis-1,4-pentadiene structure. Its presence in living organisms has been confirmed in animals and plants.

In plants, for example, its presence has been recognized in soybeans, seeds of flaxes, alfalfa, barley, broad beans, lupines, lentils, field peas, rhizomes of potatoes, wheat, apples, baker's yeast, cotton, roots of cucumbers, gooseberries, grapes, pears, beans, rice bran, strawberries, sunflowers, tea leaves and the like.

Lipoxygenase as used herein may be of any origin so long as it can introduce a hydroxyperoxy group into position 9 of α-linolenic acid. In conducting the above-mentioned lipoxygenase treatment using α-linolenic acid as the substrate it is of course preferred to let the enzymatic reaction proceed at an optimum temperature and an optimum pH of the lipoxygenase used. The lipoxygenase as used herein may be one that was extracted and/or purified from an above-mentioned plant and the like in a commonly known method, or it is possible to use a commercial product.

In this manner, 9-hydroperoxy linolenic acid (9-hydroperoxy-cis-12,15-octadecadienoic acid) is prepared from α-linolenic acid.

Subsequently, the 9-hydroperoxy linolenoic acid used as the substrate is brought to the action of hydroperoxy isomerase to prepare the desired Factor C. Hydroperoxy isomerase is an enzyme having the activity of converting a hydroperoxy group to a ketol body via epoxidization. It has been found in, for example, plants such as barley, wheat, corn, cotton, egg plants, seeds of flaxes, lettuce, oats, spinach, sunflowers, and the like.

Hydroperoxy isomerase as used herein is not specifically limited so long as it can form an epoxy group by dehydrating a hydroperoxy group at position 9 of 9-hydroperoxy linolenoic acid and it can thereby give the desired Factor C by a nucleophilic reaction of $OH^-$.

In conducting the above-mentioned hydroperoxide isomerase treatment using 9-hydroperoxy linolenic acid as the substrate it is of course preferred to let the enzymatic reaction proceed at an optimum temperature and an optimum pH of the hydroperoxide isomerase used.

The hydroperoxide isomerase as used herein may be one that was extracted and/or purified from a plant mentioned above in a known method, or it is also possible to used a commercial product.

The above two-step reaction may be conducted in either a discreet manner or a continuous manner. Furthermore, it is possible to obtain Factor C by using the crude purified or purified product of the above-mentioned enzyme to proceed the above-mentioned enzymatic reaction. It is also possible to obtain Factor C by immobilizing the above-mentioned enzyme on a carrier to prepare these immobilized enzymes and then subjecting the substrate to a column treatment or a batch treatment.

It is known that in obtaining Factor C by a nucleophilic reaction (mentioned above) of $OH^-$ after an epoxy group was formed, a γ-ketol compound is formed as a byproduct in addition to an α-ketol unsaturated fatty acid depending on the manner of reaction in the neighborhood of the above epoxy group.

The byproducts such as a γ-ketol compound and the like can be readily removed by a commonly known separation method such as HPLC and the like.

A synthetic route for synthesis of Factor C by the above-mentioned enzymatic method is described as scheme (E).

SCHEME (E)

(Allene oxide)

↓ allene oxide synthase

Factor C

The preparation of Factor C by the enzymatic methods were explained in detail as above. Lipoxygenases or allene oxide synthase that convert a double bond in a fatty acid to an α-ketol structure occur widely in the yeast and angiosperms. Thus, according to the present invention the agent for inducing flower bud formation of the present invention can also be obtained by incubating a yeast mass, a vegetative body of an angiospermal plant, or a product containing the enzyme such as the homogenate, aqueous extract thereof, etc. with a fatty acid containing a double bond in a medium that is permissive for the enzymatic reaction such as an aqueous medium.

As the yeast used in this case, for example, a yeast belonging to the genus Saccharomyces such as *Saccharomyces cereviceae* may be used.

Also, as the angiosperms, as plants, for example, belonging to the subclass Archichlamydeae of the class Dictyledoneae, there are mentioned:

the family Casuarinaceae of the order Verticillatae; the families Saururaceae, Piperaceae, and Chloranthaceae of the order Piperales;

the family Salicaceae of the order Salicales;

the family Myricaceae of the order Myricales;

the family Juglandaceae of the order Juglandales;

the families Betulaceae and Fagaceae of the order Fagales;

the families Ulmaceae, Moraceae, and Urticaceae of the order Urticales;

the family Podostemaceae of the order Podostemonales;

the family Proteaceae of the order Preteales;

the families Olacaceae, Santalaceae, and Loranthaceae of the order Santalales;

the families Aristolochiaceae and Rafflesiaceae of the order Aristolochiales;

the family Balanophoraceae of the order Balanophorales;

the family Polygonaceae of the order Polygonales;

the families Chenopodiaceae, Amaranthaceae, Nyctaginaceae, Cynocrambaceae, Phytolaccaceae, Aizoaceae, Portulacaceae, Basellaceae, and Caryophyllaceae of the order Centrospermae;

the families Magnoliaceae, Trochodendraceae, Cercidiphyllaceae, Nymphaeaceae, Ceratophyllaceae, Ranunculaceae, Lardizabalaceae, Berberidaceae, Menispermaceae, Calycanthaceae, Myristicaceae, and Lauraceae of the order Ranales;

the families Papaveraceae, Capparidaceae, Cruciferae, and Resedaceae of the order Rhoeadales;

the families Droseraceae and Nepenthaceae of the order Sarraceniales;

the families Crassulaceae, Saxifragaceae, Pittosporaceae, Hamamelidaceae, Platanaceae, Rosaceae, and Leguminosae of the order Rosales;

the families Oxalidaceae, Geraniaceae, Tropaeolaceae, Linaceae, Erythroxylaceae, Zygophyllaceae, Rutaceae, Simaroubaceae, Bruseraceae, Meliaceae, Polygalaceae, Euphorbiaceae, and Callitrichaceae of the order Geraniales;

the families Buxaceae, Empetraceae, Coriariaceae, Anacardiaceae, Aquifoliaceae, Celastraceae, Staphyleaceae, Icacinaceae, Aceraceae, Hippocastanaceae, Sapindaceae, Sabiaceae, and Balsaminaceae of the order Sapindales;

the families Rhamnaceae and Vitaceae of the order Rhamnales;

the families Elaeocarpaceae, Tiliaceae, Malvaceae, and Sterculiaceae of the order Malvales;

the families Actinidiaceae, Theaceae, Guttiferae, Elatinaceae, Tamaricaceae, Violaceae, Flacourtiaceae, Stachyuraceae, Passifloraceae, and Begoniaceae of the order Parietales;

the family Cactaceae of the order Opuntiales;

the families Thymelaeaceae, Elaegnaceae, Lythraceae, Punicaceae, Rhizophoraceae, Alangiaceae, Combretaceae, Myrtaceae, Melastomataceae, Hydrocaryaceae, Oenotheraceae, Haloragaceae, and Hippuridaceae of the order Myrtiflorae; and the families Araliaceae, Umbelliferae, and Cornaceae of the order Umbellifloraea.

Also, as plants belonging to the subclass Symperalea of the class Dictyledoneae, there are mentioned:

the family Diapensiaceae of the order Diapensiales;

the families Clethraceae, Pyrolaceae, and Ericaceae of the order Ericales;

the families Myrsinaceae and Primulaceae of the order Primulales;

the family Plumbaginaceae of the order Plumbaginales;

the families Ebenaceae, Symplocaceae, and Styracaceae of the order Ebenales;

the families Oleaceae, Loganiaceae, Gentianaceae, Apocynaceae, and Asclepiadaceae of the order Contoratae;

the families Convolvulaceae, Polemoniaceae, Boraginaceae, Verbenaceae, Labiatae, Solanaceae, Scrophulariaceae, Bignoniaceae, Pedaliaceae, Martyniaceae, Orobanchaceae, Gesneriaceae, Lentibulariaceae, Acanthaceae, Myoporaceae, and Phrymaceae of the order Tubiflorae;

the family Plantaginaceae of the order Plantaginales;

the families Rubiaceae, Caprifoliaceae, Adoxaceae, Valerianaceae, and Dipsacaceae of the order Rubiales;

the family Cucurbitaceae of the order Cucurbitales; and the families Campanulaceae and Compositae of the order Campanulatae.

Furthermore, as plants belonging to the class Monocotyledoneae, there are mentioned:

the families Typhaceae, Pandanaceae, and Sparganiaceae of the order Pandanales;

the families Potamogetonaceae, Najadaceae, Scheuchzeriaceae, Alismataceae, and Hydrocharitaceae of the order Helobiae;

the family Triuridaceae of the order Triuridales;

the families Gramineae and Cyperaceae of the order Glumiflorae;

the family Palmae of the order Plamales;

the families Araceae and Lemnaceae of the order Arales;

the families Eriocaulaceae, Bromeliaceae, Commelinaceae, Pontederiaceae, and Philydraceae of the order Commelinales;

the families Juncaceae, Stemonaceae, Liliaceae, Amaryllidaceae, Dioscoreaceae, and Iridaceae of the order Liliiflorae;

the families Musaceae, Zingiberaceae and Cannaceae of the order Scitamineae; and the families Burmanniaceae and Orchidaceae of the order Orchidales.

These plants are used in the form of a vegetative body, seeds, and the treated products thereof that were treated in various ways without inactivating enzymes, such as a dried product, a homogenate, an aqueous extract, a pressed juice, and the like. Specifically, since chlorophill is known as an inhibitor of lipoxygenase, it is preferred to use the part (seeds) containing no chlorophyll such as wheat, rice, barley, soybeans, corn, beans, and the like.

Furthermore, as in the case of the enzymatic production of Factor C, the enzyme products of lipoxygenase and hydroperoxide isomerases can be used in addition of the above-mentioned plants and the treated products thereof.

Lipoxygenase introduces a hydroperoxy group using as the substrate a highly unsaturated fatty acid having a cis, cis-1,4-pentadiene structure in the following reaction.

Thus, any fatty acids having the above structure in their carbon chain may be used as a fatty acid for the enzymatic method of the present invention. Such fatty acids include, for example, cis-9,12-octadecadienoic acid (linolenic acid; C18:2, cis-9,12), trans-9,12-octadecadienoic acid (linolelaidic acid; C18:2, trans-9,12), 9,11-(10,12)-octadecadienoic acid (C18:2, Δ9,11(10,12)), cis-6,9,12-octadecatrienoic acid (γ-linolenic acid; C18:3, cis-6,9,12), cis-9,12,15-octadecadienoic acid (linolenic acid; C18:3, cis-9,12,15), trans-9,12,15-octadecatrienoic acid (linolenelaidic acid; C18:3, trans 9,12,15), cis-6,9,12,15-octadecatrienoic acid (C18:4, cis-6,9,12,15), cis-11,14-eicosadienoic acid (C20:2, cis-11,14), cis-5,8,11-eicosatrienoic acid (C20:3, cis-5,8,11), 5,8,11-eicosatrienoic acid (C20:3, 5,8,11-ynoic), cis-8,11,14-eicosatrienoic acid (C20:3, cis-8,11,14), 8,11,14-eicosatrienoic acid (C20:3, 8,11,14-ynoic), cis-11,14,17-eicosatrienoic acid (C20:3, cis-11,14,17), cis-5,8,11,14-eicosatetraenoic acid (arachidonic acid; C20:4, cis-5,8,11,14), cis-5,8,11,17-eicosapentaenoic acid (C20:5, cis-5,8,11,14), cis-13,16-docosadienoic acid (C22:2, cis-13,16), cis-13,16,19-docosatrienoic acid (C22:3, cis-13,16,19), cis-7,10,13,16-doxosatetraenoic acid (C22:4, cis-7,10,13,16), cis-7,10,13,16,19-doxosapentaenoic acid (C22:5, cis-7,10,13,16,19), cis-4,7,10,13,16,19-docosahexaenoic acid (C22:6, cis-4,7,10,13,16,19) and the like.

Fatty acids can be selected depending on the kind of the fatty acid to be produced. For example, in order to obtain 9-hydroperoxy-10(E),12(Z),15(Z)-octadecatrienoic acid and 13-hydroperoxy-9(Z),11(E),15(Z)-octadecatrienoic acid belonging to the third embodiment of the present invention by the enzymatic method, it is only required to bring linolenic acid to the action of lipoxygenase. When hydroperoxide isomerase is further used, as described above, Factor C can be obtained.

By further bringing Factor C to the action of lipoxygenase, 9-hydroxy-10-oxo-13-hydroperoxy-11(E),15(Z)-octadecadienoic acid can be obtained. By further bringing 13-hydroxy-12-oxo-9(Z),15(Z)-octadecadienoic acid to the action of lipoxygenase, 9-hydroperoxy-12-oxo-13-hydroxy-10(E),15(Z)-octadecadienoic acid can be obtained.

Incubation of an enzyme, a yeast mass or a vegetative body or the treated products thereof with a fatty acid is conducted as described above for the enzymatic production of Factor C.

Also, Factor C can be obtained by the chemical synthetic reactions in addition to the above-mentioned extraction methods and the enzymatic methods.

On the other hand, norepinephrine that exhibits the desired effect of inducing flower bud formation in combination with an unsaturated fatty acid of the present invention may be the one that was synthesized by a commonly known method, or it is of course possible to use a commercial product.

According to the present invention, the (+) type norepinephrine in addition to the naturally occurring (−) type norepinephrine or mixtures thereof may be used.

The agents for inducing flower bud formation of the present invention (hereinafter referred to as the invention agents for inducing flower bud formation) thus produced having as active ingredients an unsaturated fatty acid or an unsaturated fatty acid and norepinephrine are provided.

Among the invention agents for inducing flower bud formation, those having an unsaturated fatty acid as the sole active ingredient are intended to exhibit the desired effect of inducing flower bud formation in combination with norepinephrine potentially present in plants, or to exhibit the desired effect of inducing flower bud formation by combining this form of the invention agent for inducing flower bud formation with a norepinephrine agent depending on the kind and state of the plants.

Furthermore, among the invention agents for inducing flower bud formation, those forms having an unsaturated fatty acid and norepinephrine as the active ingredients can be conveniently used by blending the above active ingredients in such a ratio that exhibits the most intense effect of inducing flower bud formation of the invention agents for inducing flower bud formation.

The ratio of blending an unsaturated fatty acid and norepinephrine in the invention agent for inducing flower bud formation can be adjusted as appropriate depending on, but not limited to, the above-mentioned purpose and furthermore the property of the plant used. When the presence of norepinephrine is not taken into consideration, as, For example, in the plants of the family Lemnaceae such as *Lemna paucicostata*, the equimolar blending of the two (an unsaturated fatty acid and norepinephrine) is preferred in that it can exhibit more effectively the desired effect of the present invention. When the two are not blended in equimolar amounts for Lemna plants, the effect exhibited tends to be almost equal to the effect that would be exhibited when the two are blended at a concentration of the ingredient contained in a smaller amount.

The invention agents for inducing flower bud formation are in most cases more effective when administered while treating the subject plants depending on the property of the plants. For example, in the ratio of short-day plants such as *Pharbitis nil*, strain Violet described below in Examples etc., it is more effective to conduct a certain dark treatment prior to using the invention agents for inducing flower bud formation.

The above active ingredients may be used as they are as the invention agents for inducing flower bud formation, but they may be blended as appropriate depending on the desired dosage form applicable to plants, for example a pharmaceutically applicable known carrier ingredient such as a liquid, a solid, a powder, an emulsion, a low-floor additive, etc. and an adjuvant etc. in the range that does not hinder the desired effect of inducing flower bud formation. For example, as the carrier ingredients when the invention agent for inducing flower bud formation is a low-floor additive or a solid, mostly inorganic materials such as talc, clay, vermiculite, diatomaceous earth, kaolin, calcium carbonate, calcium hydroxide, white clay, silica gel etc., and solid carriers such as wheat flour, starch, etc.: or when it is a liquid, mostly water, aromatic hydrocarbons such as xylene etc., alcohols such as ethanol, ethylene glycol, etc., ketones such as acetone, ethers such as dioxane, tetrahydrofuran, etc., dimethylformamide, dimethyl sulfoxide, acetonitrile, etc. are used as the above-mentioned carrier ingredient. As pharmaceutical adjuvants, for example, anionic surfactants such as alkyl sulfate esters, alkyl sulfonates, alkylaryl sulfonates, dialkylsulfo succinates, etc., cationic surfactants such as higher aliphatic amines etc., nonionic surfactants such as polyoxyethylene glycol alkyl ether, polyoxyethylene glycol acyl ester, polyoxyethylene glycol polyhydric alcohol acyl ester, cellulose derivatives, etc., thickeners such as gelatin, casein, gum Arabic, etc., bulking agents, binders, etc. can be blended as appropriate.

Furthermore, as needed, plant growth-control agents such as benzoic acid, nicotinic acid, nicotinamide, pipecolic acid, or the like can be blended into the invention agents for inducing flower bud formation so long as it does not affect the above-mentioned desired effect of the present invention.

The invention agents for inducing flower bud formation mentioned above may be used for a variety of plants in a manner suitable for the dosage form. According to the present invention, for example, it is possible to effect spraying, dropping, applying, and so on of the inducers as a liquid or an emulsion onto the meristem, the surface and/or the back surface of leaves of the plant to be flowered, the entire plant and the like, or to effect absorption from the soil by the root as a solid or a powder. When the plant to be flowered is a water plant such as *Lemna paucicostata*, it is also possible to effect absorption from the root as a low-floor additive or gradual dissolution of the solid in the water.

According to the present invention, a kit for inducing flower bud formation that takes a form of a kit containing Factor C which is an active ingredient mentioned above, an unsaturated fatty acid, and norepinephrine is also provided. The purpose and effects of said kit for inducing flower bud formation are the same as those mentioned above for the invention agents for inducing flower bud formation.

The types of plants to which the invention agents for inducing flower bud formation or the kit for inducing flower bud formation can be applied are not specifically limited and the invention agents for inducing flower bud formation are effective for both dicotyledons and monocotyledons.

As the dicotyledons, there are mentioned the plants of, for example, the family Convolvulaceae including the genus Pharbitis (*Pharbitis nil*, strain Violet), the genus Calystegia (*C. japonica, C. hederacea, C. soldanella*), genus Ipomoea (*I. pes-caprae, I. batatas*), and the genus Cuscuta (*C. japonica, C. australis*), the family Casuarinaceae, the family Saururaceae, the family Piperaceae, the family Chloranthaceae, the family Salicaceae, the family Myricaceae, the family Juglandaceae, the family Betulaceae, the family Fagaceae, the family Ulmaceae, the family Moraceae, the family Urticaceae, the family Podostemaceae, the family Proteaceae, the family Olacaceae, the family Santalaceae, the family Loranthaceae, the family Aristolochiaceae, the family Rafflesiaceae, the family Balanophoraceae, the family Polygonaceae, the family Chenopodiaceae, the family Amaranthaceae, the family Nyctaginaceae, the family Cynocrambaceae, the family Phytolaccaceae, the family Aizoaceae, the family Portulacaceae, the family Basellaceae, the family Caryophyllaceae, the family Magnoliaceae, the family Trochodendraceae, the family Cercidiphyllaceae, the family Nymphaeaceae, the family Ceratophyllaceae, the family Ranunculaceae, the family Lardizabalaceae, the family Berberidaceae, the family Menispermaceae, the family Calycanthaceae, the family Lauraceae, the family Papaveraceae, the family Capparidaceae, the family Cruciferae, the family Droseraceae, the family Nepenthaceae, the family Crassulaceae, the family Saxifragaceae, the family Pittosporaceae, the family Hamamelidaceae, the family Platanaceae, the family Rosaceae, the family Leguminosae, the family Oxalidaceae, the family Geraniaceae, the family Linaceae, the family Zygophyllaceae, the family Rutaceae, the family Simaroubaceae, the family Bruseraceae, the family Meliaceae, the family Polygalaceae, the family Euphorbiaceae, the family Callitrichaceae, the family Buxaceae, the family Empetraceae, the family Coriariaceae, the family Anacardiaceae, the family Aquifoliaceae, the family Celastraceae, the family Staphyleaceae, the family Icacinaceae, the family Aceraceae, the family Hippocastanaceae, the family Sapindaceae, the family Sabiaceae, the family Balsaminaceae, the family Rhamnaceae, the family Vitaceae, the family Elaeocarpaceae, the family Tiliaceae, the family Malvaceae, the family Sterculiaceae, the family Actinidiaceae, the family Theaceae, the family Guttiferae, the family Elatinaceae, the family Tamaricaceae, the family Violaceae, the family Flacourtiaceae, the family Stachyuraceae, the family Passifloraceae, the family Begoniaceae, the family Cactaceae, the family Thymelaeaceae, the family Elaegnaceae, the family Lythraceae, the family Punicaceae, the family Rhizophoraceae, the family Alangiaceae, the family Melastomataceae, the family Hydrocaryaceae, the family Oenotheraceae, the family Haloragaceae, the family Hippuridaceae, the family Araliaceae, the family Umbelliferae, the family Cornaceae, the family Diapensiaceae, the family Clethraceae, the family Pyrolaceae, the family Ericaceae, the family Myrsinaceae, the family Primulaceae, the family Plumbaginaceae, the family Ebenaceae, the family Symplocaceae, the family Styracaceae, the family Oleaceae, the family Loganiaceae, the family Gentianaceae, the family Apocynaceae, the family Asclepiadaceae, the family Polemoniaceae, the family Boraginaceae, the family Verbenaceae, the family Labiatae, the family Solanaceae, the family Scrophulariaceae, the family Bignoniaceae, the family Pedaliaceae, the family Orobanchaceae, the family Gesneriaceae, the family Lentibulariaceae, the family Acanthaceae, the family Myoporaceae, the family Phrymaceae, the family Plantaginaceae, the family Rubiaceae, the family Caprifoliaceae, the family Adoxaceae, the family Valerianaceae, the family Dipsacaceae, the family Cucurbitaceae, the family Campanulaceae, the family Compositae, and the like.

Furthermore, as monocotyledons there are mentioned the plants of the family Lemnaceae including the genus Spirodela (*S. polyrhiza*) and the genus Lemna (*L. paucicostata, L. trisulca*), the family Typhaceae, the family Sparganiaceae, the family Potamogetonaceae, the family Najadaceae, the family Scheuchzeriaceae, the family Alismataceae, the family Hydrocharitaceae, the family Triuridaceae, the family Gramineae, the family Cyperaceae, the family Palmae, the family Araceae, the family Eriocaulaceae, the family Commelinaceae, the family Pontederiaceae, the family Juncaceae, the family Stemonaceae, the family Liliaceae, the family Amaryllidaceae, the family Dioscoreaceae, the family Iridaceae, the family Musaceae, the family Zingiberaceae, the family Cannaceae, the family Burmanniaceae, the family Orchidaceae, and the like.

EXAMPLES

The present invention will now be explained more specifically with the following examples. It should be understood, however, that these examples do not limit the technical scope of the present invention in any way.

Example 1

Preparation of Factor C by the Extraction Method

*Lemna paucicosta* strain 441 (hereinafter referred to as "P441"; this strain was obtained from Atushi Takimoto, professor emeritus of Kyoto University, Faculty of Agriculture, who is one of the inventors of the present invention; the strain is available on request) was aseptically subcultured in the 1/2 diluted Hutner's medium [Hutner 1953; the composition of the undiluted Hutner's medium is $KH_2PO_4$ (400 mg), $NH_4NO_3$ (200 mg), EDTA.2K (690 mg), $Ca(NO_3)_2.4H_2O$ (354 mg), $MgSO_4.7H_2O$ (500 mg), $FeSO_4.7H_2O$ (24.9 mg), $MnCl_2.4H_2O$ (17.9 mg), $ZnSO_4.7H_2O$ (65.9 mg), $CaSO_4.5H_2O$ (3.95 mg), $Na_2MoO_4.2H_2O$ (14.2 mg), $H_3BO_3$ (14.2 mg), $Co(Mo_3)_2.6H_2O$ (0.2 mg)/1000 ml distilled water, pH 6.2 to 6.4] containing 1% sucrose under continuous illumination by a daylight fluorescent lamp (illuminated to the plant at a rate of about 5 W/m² using Hitachi FL20 SSD) at 24 to 25° C.

Then after washing the culture of P441 in distilled water it was transferred to 1/10 diluted E medium [Cleland and Briggs 1967; the composition of the 1/10 E medium is $Ca(NO_3)_2.4H_2O$ (118 mg), $MgSO_4.7H_2O$ (40.2 mg), $KH_2PO_4$ (68.0 mg), $KNO_3$ (115 mg), $FeCl_3.6H_2O$ (0.54 mg), tertarate (0.30 mg), $H_3BO_3$ (0.29 mg), $ZnSO_4.7H_2O$ (0.022 mg), $Na_2MoO_4.2H_2O$ (0.013 mg), $CuSO_4.5H_2O$ (0.008 mg), $MnCl_2.4H_2O$ (0.36 mg), EDTA-2K (1.21 mg), EDTA.NaFe(III) salt (0.77 mg)/1000 ml distilled water], and was aseptically cultured under continuous illumination by a daylight fluorescent lamp (about 5 W/m²) at 24 to 25° C. for 6 to 12 days.

The thus prepared P441 culture was subjected to a drought stress by leaving it spread out on a dry filter paper at a low humidity (a relative humidity of 50% or less) at about 24 to 25° C. for 15 minutes.

The drought stress-treated P441 (75 g) was immersed in 1.5 liter of distilled water at 24 to 25° C. for 2 hours.

The P441 was then removed from the above immersing solution and 1.5 liter of chloroform was added in three portions to said immersing solution to extract. The chloroform layer obtained was washed with water, and then 0.1 ml of acetic acid was added thereto followed by evaporation to dryness. To the residue 500 μl of methanol was added to dissolve the residue.

Subsequently the above methanol solution was subjected to high performance liquid chromatography [column: ODS (octadecylsilane) column (Φ 10×250 mm, CAPCELLPAK C18: manufactured by Shiseido Co., Ltd.); solvent: 50% distilled water containing 0.1% trifluoroacetic acid and 50% acetonitrile containing 0.085% trifluoroacetic acid as the mobile phase at a flow rate of 4.00 ml/min to collect the active fractions (the activity was measured in the method similar to the one in the test example described below] and fractions at an elution time of about 15 minutes were collected.

To the active fractions thus collected, ethyl acetate was added and the ethyl acetate layer was separated and then was washed with water, followed by evaporation of this ethyl acetate to dryness to obtain about 1 mg of the desired purified product as a dry solid.

In order to determine the structure of the dry solid the chemical shifts thereof were measured using $^{13}$C-NMR (the above dry solid was dissolved in a mixture of one drop each of methyl alcohol-d4 and acetic acid-d4 to make a sample for measurement).

Figure 1:
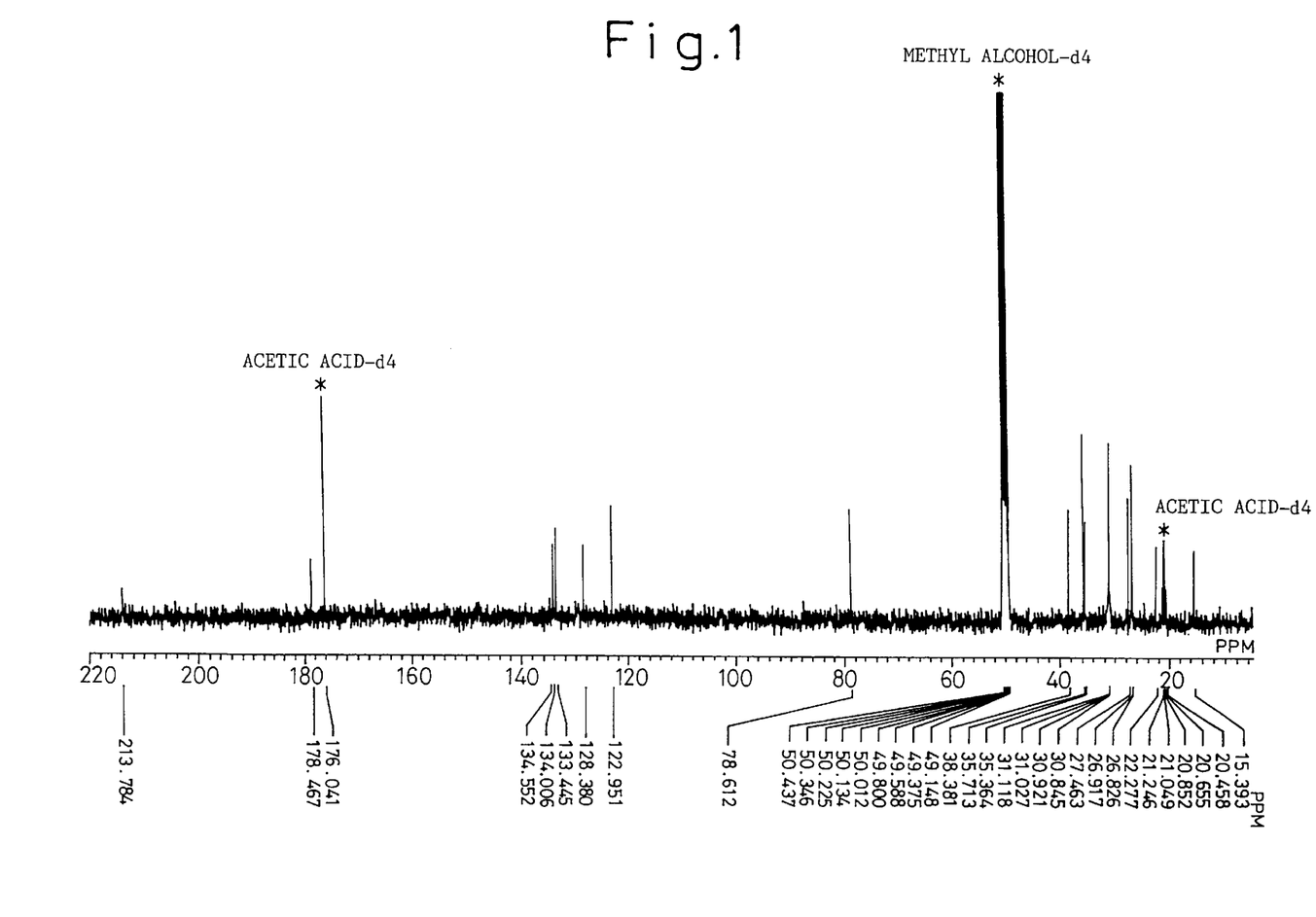
FIG. 1 shows a chart of $^{13}$C-NMR showing Factor C.

As a result, the chemical shifts and the chemical structural formula characterized by the chemical shifts were determined as follows:

1: 178.47(s), 2: 35.71(t), 3: 26.82*(t), 4: 31.11(t), 5: 26.92*(t), 6: 35.36(t), 7: 78.61(d), 8: 213.78(s), 9: 38.38(t), 10: 122.95(d), 11: 133.45(d), 12: 27.46(t), 13: 128.38(d), 14: 134.55(d), 15: 22.28(t), 16: 15.39(q) (See FIG. 1 for the chart; each number at the head of the chemical shift corresponds the circled number representing each carbon atom in the chemical structural formula below).

means that its assignment has not been known.

($C_{18}H_{30}O_4$, M.W.: 310)

The result evidently revealed that the dry solid is the desired purified α-ketol unsaturated fatty acid (Factor C).

Example 2

The Effect of Factor C of Inducing Flower Bud Formation in *Lemna paucicostata*

The effect of Factor C obtained in the preparation example above of inducing flower bud formation was evaluated using the P151 strain of *Lemna paucicostata* (hereinafter referred to as "P151"; this strain was obtained from Atushi Takimoto, professor emeritus of Kyoto University Faculty of Agriculture, who is one of the inventors of the present invention; the strain is available on request) as a model plant in terms of its rate of flower formation (%) (the number of thalluses for which flower formation was observed/the total number of thalluses×100).

Thus, 0.155 mg of the above-mentioned Factor C was dissolved in 0.15 ml of water, to which were added 50 μl of 10 mM norepinephrine and 25 μl of 0.5M tris buffer, pH 8.0. The solution was incubated at 25° C. for six hours.

Then in order to obtain Factor C and norepinephrine in the concentrations shown in Table 1, the solution incubated under the condition mentioned above was added to 10 ml of the assay medium (1/10 E medium+1 μm benzyladenine, but with no addition of sugar) in a 30 ml flask. The results are shown in Table 2.

TABLE 1

|   | NEeq | | FCeq | |   | NEeq | | FCeq | |
| --- | --- | --- | --- | --- | --- | --- | --- | --- | --- |
| A | 0.3 | μM | 7.8 | nM | D | 0.3 | μM | 2.9 | nM |
| A | 3 | μM | 78 | nM | D | 3 | μM | 29 | nM |
| A | 10 | μM | 260 | nM | D | 10 | μM | 98 | nM |
| B | 0.3 | μM | 78 | nM | E | 0.3 | μM | 29 | nM |
| B | 3 | μM | 780 | nM | E | 3 | μM | 290 | nM |
| B | 10 | μM | 2.6 | mM | E | 10 | μM | 980 | nM |
| C | 30 | nM | 78 | nM | F | 30 | nM | 29 | nM |
| C | 100 | nM | 260 | nM | F | 100 | nM | 98 | nM |
| C | 0.3 | μM | 780 | nM | F | 0.3 | μM | 29 | nM |
| C | 3 | μM | 7.8 | μM | F | 3 | μM | 2.9 | μM |
| C | 10 | μM | 26 | μM | F | 10 | μM | 9.8 | μM |

One colony each of P151 was inoculated to the assay medium to which each concentration of Factor C was added and cultured under continuous illumination by a daylight fluorescent lamp (illuminated to the plant at a rate of about 5 W/m² using Hitachi FL20 SSD) at 24 to 25° C. for seven days to determine the rate of flower formation mentioned above (Table 2).

The tests for the same system were conducted in three flasks and the test for the same system was conducted at least twice. The results shown in Table 2 are the mean of each test ±SE (standard error).

TABLE 2

|   | 30 nM NE | 100 nM NE | 0.3 μM NE | 3.0 μM NE | 10 μM NE |
| --- | --- | --- | --- | --- | --- |
| A | — | — | 1.6 ± 1.6 | 29.5 ± 3.5 | 51.5 ± 2.4 |
| B | — | — | 29.0 ± 10.3 | 34.7 ± 4.4 | 44.8 ± 0.7 |
| C | 3.0 ± 3.0 | 40.6 ± 2.1 | 46.3 ± 3.6 | 56.2 ± 1.2 | 53.2 ± 1.1 |
| D | — | — | — | 16.3 ± 6.4 | 50.6 ± 7.0 |
| E | — | — | 1.9 ± 1.1 | 61.6 ± 1.2 | 65.0 ± 0.4 |
| F | 11.7 ± 2.7 | 39.2 ± 7.9 | 63.2 ± 1.2 | 60.8 ± 1.9 | 66.8 ± 3.5 |

The result evidently revealed that the activity of inducing flower bud formation increases largely in a dose-dependent manner, and that in the experiment groups C and F in which Factor C content was equimolar to that of norepinephrine or higher, the activity of inducing flower bud formation appears even at such an extremely low concentration of 30 nM of norepinephrine.

In other words, it was revealed that when the Factor C content is equimolar to that of norepinephrine, the desired activity of inducing flower bud formation in *Lemna paucicostata* is most efficiently exhibited.

Thus, the activity of inducing flower bud formation by the combined administration of Factor C and norepinephrine at the above concentrations was observed.

Furthermore, as explained below, since the activity of inducing flower bud formation by Factor C is observed in *Pharbitis nil*, strain Violet that is a dicotyledon strain entirely different from that of monocotyledonous *Lemna paucicostata*, it is evident that the activity of inducing flower bud formation will be observed in the plants of the family Lemnaceae including the genus Spirodela and the genus Lemna.

Example 3

The Effect of Factor C of Inducing Flower Bud Formation in *Pharbitis nil*, Strain Violet Nine grams of the seeds of *Pharbitis nil*, strain Violet were treated with concentrated sulfuric acid for 20 minutes and then left under running water overnight. Then, the seeds were placed in the damp sea sand with the navel part of the seeds facing upward to radicate. These radicated seeds were planted in sea sands at a depth of about 1.5 to 2.0 cm and were cultured under continuous illumination (about 5 days).

*Pharbitis nil*, strain Violet of which leaves were just unfolded by the cultivation was transferred to the culture liquid [$KNO_3$ (250 mg), $NH_4NO_3$ (250 mg), $KH_2PO_4$ (250 mg), $MgSO_4.7H_2O$ (250 mg), $MgSO_4.4H_2O$ (1 mg), Fe-citrate n-hydrate (6 mg), $H_3BO_3$ (2 mg), $CuSO_4.5H_2O$ (0.1 mg), $ZnSO_4.7H_2O$ (0.2 mg), $Na_2MoO_4.2H_2O$ (0.2 mg), $Ca(H_2PO_4)_2.2H_2O$ (250 mg)/1000 ml distilled water].

The culture system was subjected to the dark treatment with giving the test drugs such as Factor C obtained in the above preparation example directly to the hypocotyl of *Pharbitis nil*, strain Violet through cotton threads, and then was grown under continuous illumination at 28° C. for 16 days and on day 16 the number of flower buds were confirmed by observation using the stereomicroscope.

The dark treatment was conducted overnight (16 hours of dark treatment) or for two nights (16 hours of dark treatment+8 hours of light treatment+16 hours of dark treatment).

Figure 2:
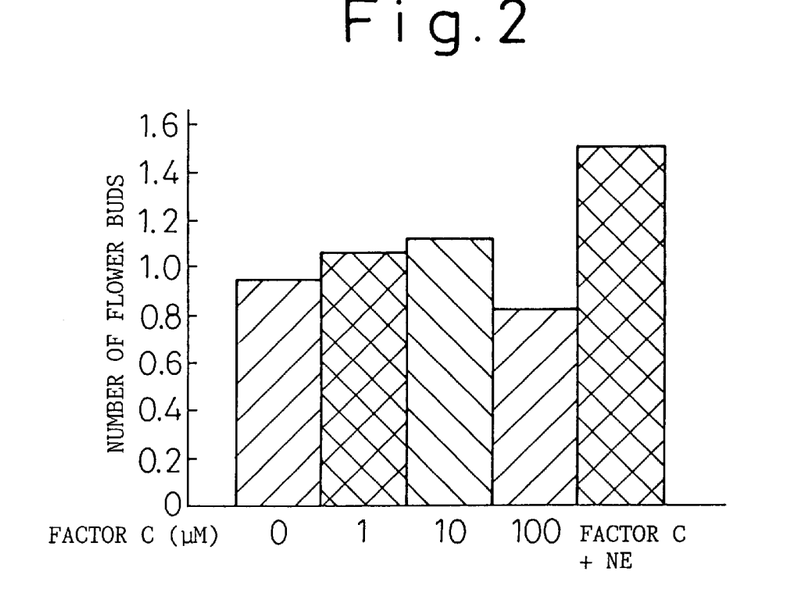
FIG. 2 is a drawing showing the effect of inducing flower bud formation of *Pharbitis nil*, strain Violet by Factor C when *Pharbitis nil*, strain Violet was subjected to overnight dark treatment.
Figure 3:
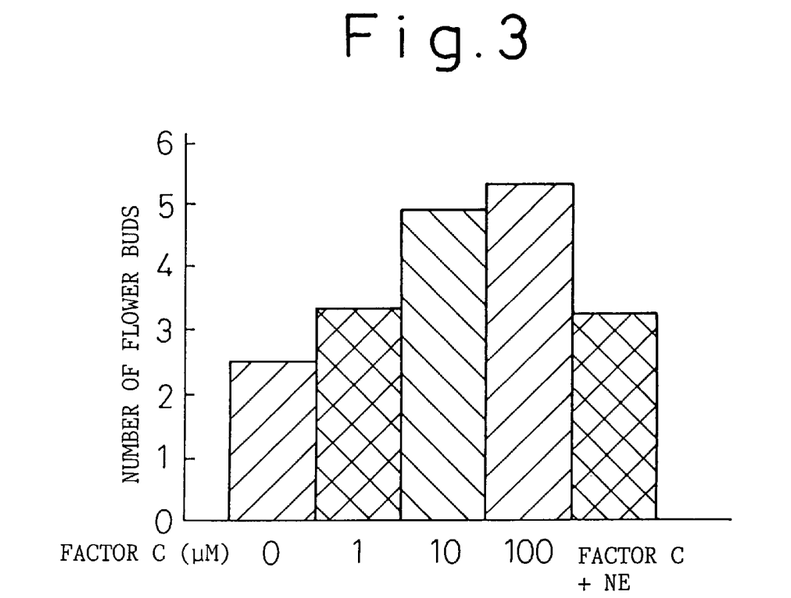
FIG. 3 is a drawing showing the effect of inducing flower bud formation of *Pharbitis nil*, strain Violet by Factor C when *Pharbitis nil*, strain Violet was subjected to the dark treatment for two nights.

The result of the overnight treatment is shown in FIG. 2, and the result of the two-night treatment is shown in FIG. 3.

In both figures, the control group is the group that was given distilled water; 1 μM (FC), 10 μM (FC), and 100 μM (FC) are the group that received each concentration of Factor C in the WS (water stressed); and Factor C+NE means that 10 μM norepinephrine was incubated with the WS containing WμM Factor C. The WS means the immersing water of the *Lemna paucicostata* P441 strain that was subjected to dry stress by the method described in the test example 1.

Though the activity of Factor C of inducing flower bud formation was observed for the overnight treatment group as compared to the control group as is shown in FIG. 2, a stronger activity of inducing flower bud formation was observed when administered in combination with norepinephrine.

In contrast, when attention is paid to the control group or the difference in the concentration of drugs, the average number of flower buds increased in a dose-dependent manner in the two-night dark treatment group shown in FIG. 3 indicating at least an enhanced activity of inducing flower bud formation.

Thus, the activity of Factor C of inducing flower bud formation in *Pharbitis nil*, strain Violet was observed.

As described above, since the activity of inducing flower bud formation is observed in *Lemna paucicostata* that is a strain entirely different from that of *Pharbitis nil*, strain Violet, it is evident that the activity of inducing flower bud formation will be observed in the plants of the family Convolvulaceae including the genus Pharbitis, the genus Calystegia, the genus Ipomoea and the genus Cuscuta.

Furthermore, as described above, since the activity of inducing flower bud formation was observed for both monocotyledons and dicotyledons that are entirely different strains from each other by giving Factor C etc., it was strongly suggested that the activity of inducing flower bud formation will be observed for plants in general by the administration of Factor C.

Example 4

Figure 4:
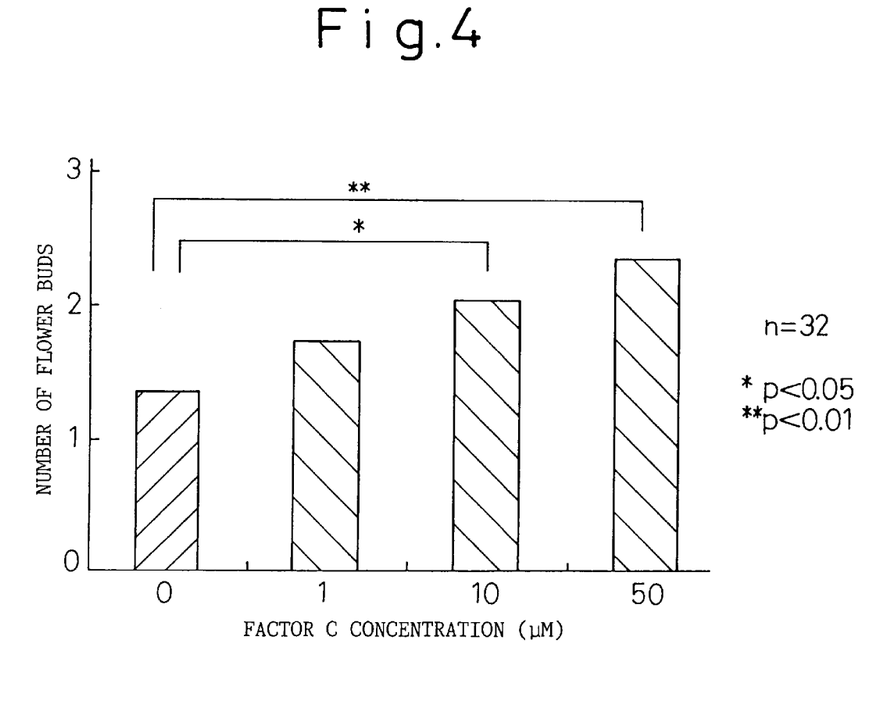
FIG. 4 is a drawing showing the effect of inducing flower bud formation of *Pharbitis nil*, strain Violet by Factor C.

*Pharbitis nil*, strain Violet germinated as described in Example 3 was prepared. Separately, an aqueous solution of Factor C at a concentration of 1 μM, 10 μM or 50 μM was prepared, which was sprayed onto both of the upper and the lower of the cotyledons immediately prior to the dark treatment and daily for 10 days after the dark treatment. The number of flower buds on day 14 is shown in FIG. 4. Thus, an activity of inducing flower bud was also evidently observed by the method of spraying Factor C on the leaves.

Example 5

Twenty pots of *Dendrobium hybridum* Hort. Redstar were cultivated by giving as appropriate oil cake and a liquid fertilizer (Hyponex) from April to July. After stopping fertilization, from August to December the plants were grouped into the experimental group and the control one. For the experimental group cultivation was continued by spraying an aqueous solution of 50 μM Factor C on the entire plant daily from Monday through Friday every week. Dendrobium was kept in the greenhouse in order not to bring the lowest temperature fall under 10° C. even in winter. The control group was treated similarly using water.

The results are shown in Table 3.

TABLE 3

| | Time of flowering | Relative value of number of flowerings per plant |
| --- | --- | --- |
| Experiment | February (7 pots), March (3 pots) | 132 |
| Control (water) | March (8 pots), April (2 pots) | 100 |

As described above, Factor C promoted the flower bud formation of *Dendrobium hybridum* Hort. Redstar.

Example 6

Twenty pots of *Cymbidium hybridum* Hort. Raspberry Mille-feuille were cultivated by giving as appropriate oil cake and a liquid fertilizer (Hyponex) from April to August. After stopping fertilization, from September to November the plants were grouped into the experimental group and the control group. For the experimental group, cultivation was continued by spraying an aqueous solution of 50 μM Factor C on the entire plant daily from Monday through Friday every week. The control group was treated similarly using water. Cymbidium was kept in the greenhouse in order not to bring the lowest temperature fall under 10° C. even in winter.

The results are shown in Table 4.

TABLE 4

| | | Relative value of number of flowerings per plant |
| --- | --- | --- |
| Experiment | January (1 pot), February (7 pots), March (2 pots) | 151 |
| Control (water) | March (10 pots) | 100 |

As described above, Factor C promoted the flower bud formation of *Cymbidium hybridum* Hort. Raspberry Mille-feuille.

Example 7

Seeds of *Dianthus caryophyllus* L were planted in September and repotted in March. After repotting, an aqueous solution of 50 μM Factor C was sprayed onto the entire plant daily from Monday through Friday every week. In July, the number of the flowered plants per 100 plants were counted. The results are shown in Table 5.

TABLE 5

| | Relative value of number of flowerings per plant |
| --- | --- |
| Experiment | 142 |
| Control (water) | 100 |

As described above, Factor C promoted the flower bud formation of *Dianthus caryophyllus* L.

Example 8

*Pharbitis nil*, strain Violet germinated as described in Example 3 was prepared. An aqueous solution of 9-hydroperoxy-10(E),12(Z),15(Z)-octadecatrienoic acid in a concentration of 10 μM, 50 μM or 100 μM was prepared, which was introduced into the hypocotyl through cotton threads similarly as described in Example 3. The number of flower buds on day 14 is shown in Table 6.

TABLE 6

|  | The number of flower buds on day 14 |
|---|---|
| Control (water) | 0.892 |
| 10 μM | 1.425 |
| 50 μM | 1.623 |
| 100 μM | 2.209 |

Mean of n=16.

Example 9

By repeating the method of Example 8, 9-hydroxy-10-oxo-13-hydroperoxy-11(E),15(Z)-octadecadienoic acid was used as the test substance. The number of flower buds on day 14 is shown in Table 7.

TABLE 7

|  | The number of flower buds on day 14 |
|---|---|
| Control (water) | 1.203 |
| 10 μM | 1.392 |
| 50 μM | 1.572 |
| 100 μM | 1.704 |

Mean of n=16.

Example 10

Preparation of Factor C by the Enzymatic Method

Non-heated wheat was ground to powder and 200 g of the powder (for soybeans, commercial products are available from Sigma) was dispersed in one liter of water. 0.5 g of linolenic acid was added thereto and incubated while stirring at 30° C. After incubation for three days, it was extracted with chloroform. After evaporating chloroform in the evaporator it was fractionated using a silica gel column (carrier: Wakogel C-200, Wako Pure Chemical Industries, Co. Ltd., Solvent: ether-benzen-ethanol-acetic acid 40:50:2:0.2) and collected.

Fractions of soybeans were similarly obtained.

In a similar manner to those described in Examples 1 to 6, each of the above fractions was confirmed to promote flower bud formation.

Example 11

Ten grams of dry soybeans that were pulverized using a mixer was taken and suspended into 10 ml of deionized water. After adding 20 mg of linolenic acid it was reacted while stirring for 2 days keeping the temperature at 30° C. The soybean powder was removed by filtration and the aqueous layer was extracted with ethyl acetate. After evaporating ethyl acetate under reduced pressure, it was dissolved again in 25 ml of water (sample A). Some were not dissolved but were used as they are.

To one ml of sample A were added 10 μl of 10 mM norepinephrine (NE) and 5 μl of 0.5 M tris buffer, pH 8.0, and then incubated overnight at 25° C. It was added to a medium for the Lemna (strain 151) so that the concentration of NE becomes 0.3 μM, 1 μM, or 3 μM. One colony of Lemna (strain 151) was planted and cultured under continuous illumination (Hitachi FL20SSD, 10 Wm$^{-2}$) for one week (25° C.).

The rate of flower bud formation was evaluated by the percentage of flower formation.

The results are shown in Table 8.

TABLE 8

|  | Concentration of NE (μM) | | |
|---|---|---|---|
|  | 0.3 | 1 | 3 |
| Linolenic acid | 0 | 0 | 0 |
| Sample A | 44.3 ± 6.5 | 58.2 ± 2.3 | 56.9 ± 4.3 |

The results are shown in the mean±SD for three samples.

As described above, it was confirmed that though linolenic acid itself has no activity of inducing flower bud formation it can be converted to a substance having the activity of promoting flower bud formation by the enzymatic treatment. The effect of using it in combination with norepinephrine was also confirmed.

Example 12

Using sample A prepared in Example 10 in a method described in Example 1, the induction of flower bud formation in *Pharbitis nil*, strain Violet was evaluated. The results are shown in Table 9 below.

TABLE 9

| Treatment | The number of flower buds of *Pharbitis nil*, strain Violet |
|---|---|
| Water | 1.3 |
| Linolenic acid | 0.9 |
| Sample A | 2.5 |

Mean of n=24

Sample A had the activity of promoting flower bud formation with a significant difference of P<0.1 as compared to water or linolenic acid.

Example 13

Threshed dry wheat was ground to powder and treated by the method described in Example 11 to obtain sample B.

Then, in a similar manner to that described in Example 11 its activity of inducing flower bud formation in *Lemna paucicostata*. The results are shown in Table 10.

TABLE 10

|  | Concentration of NE (μM) | | |
|---|---|---|---|
|  | 0.3 | 1 | 3 |
| Linolenic acid | 0 | 0 | 0 |
| sample B | 55.4 ± 2.5 | 52.9 ± 5.4 | 58.4 ± 3.6 |

As described above, the effect of the enzymatic treatment of linolenic acid and the effect of using in combination with neoepinephrine were confirmed.

Example 14

Replacing linolenic acid with arachidonic acid the method of Example 11 was repeated to obtain sample C.

Using this sample C its activity of inducing flower bud formation in *Lemna paucicostata* was evaluated by the method described in Example 11. The results are shown in Table 11.

TABLE 11

| | Concentration of NE ($\mu$M) | | |
| --- | --- | --- | --- |
| | 0.3 | 1 | 3 |
| Arachidonic acid | 0 | 0 | 0 |
| Sample C | 10.9 ± 2.3 | 27.5 ± 1.4 | 48.9 ± 2.7 |

As described above, the effect of the enzymatic treatment of arachidonic acid and the effect of using in combination with neoepinephrine were confirmed.

Example 15

Figure 5:
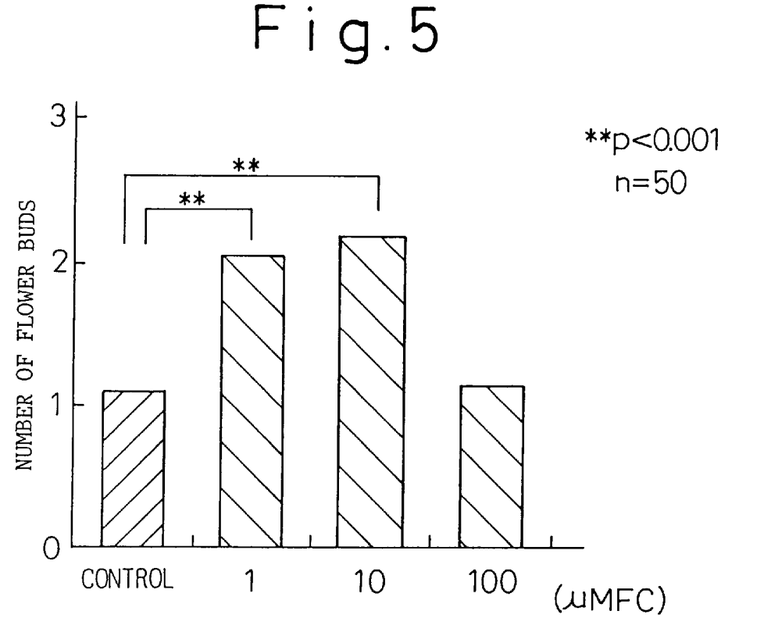
FIG. 5 is a graph showing the number of flower buds obtained when the time of dark treatment was fixed at 16 hours and the concentration of Factor C was varied.

The method of Example 3 was repeated except that the time of the dark treatment was fixed at 16 days and the number to be observed n was set at 50. The results are shown in FIG. 5. The results revealed that the number of flower buds significantly increased when the concentration of Factor C was 1 to 10 $\mu$M.

Example 16

Figure 6:
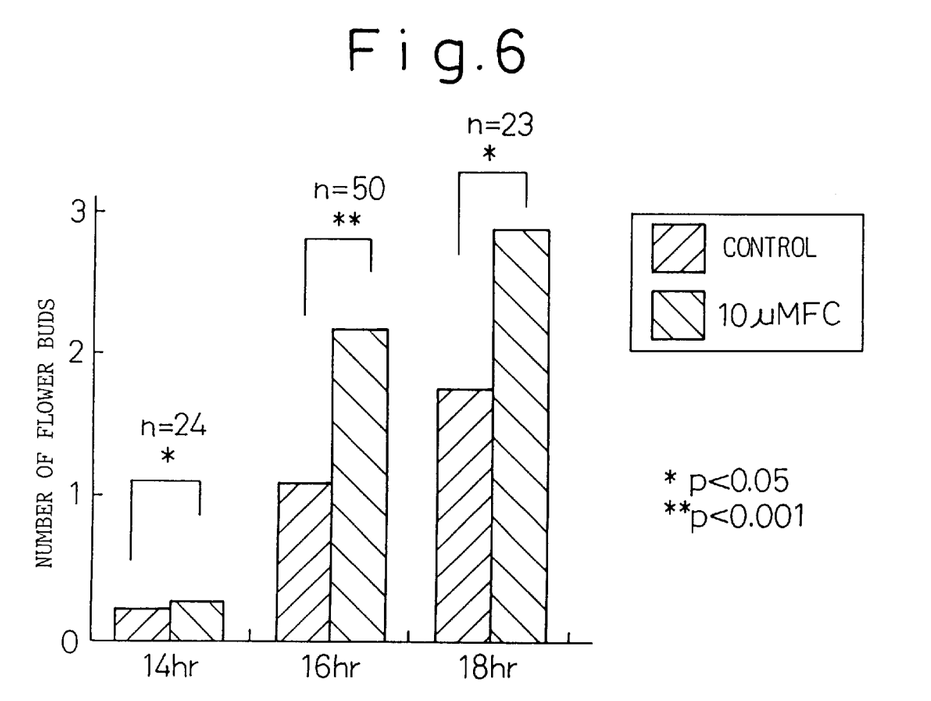
FIG. 6 is a graph showing the number of flower buds obtained when the concentration of Factor C was fixed at 10 μM and the time of the dark treatment was varied.

The method of Example 3 was repeated except that the time of the overnight dark treatment was set at 14, 16, or 18 hours and the concentration of Factor C was fixed at 10 $\mu$M. The results are shown in FIG. 6. The results evidently revealed that the number of flower buds increased by 10 mM of Factor C irrespective of the time of the dark treatment.

INDUSTRIAL APPLICABILITY

According to the present invention, the agents for inducing flower bud formation that directly affect the flower bud formation of plants and a kit for inducing flower bud formation are provided.

We claim:

1. A method for inducing flower bud formation comprising:
   applying to plants an agent for inducing flower bud formation comprising a fatty acid of 16 to 24 carbon atoms having an oxo group and a hydroxy group and containing 0 to 6 double bonds;
   wherein the oxo group and the hydroxy group in said fatty acid constitute an $\alpha$-ketol structure or a $\gamma$-ketol structure.

2. The method for inducing flower bud formation according to claim 1 wherein the number of carbon atoms in said fatty acid is 18.

3. The method for inducing flower bud formation according to claim 2 wherein said fatty acid is 9-hydroxy-10-oxo-12(Z),15(Z)-octadecadienoic acid.

4. The method for inducing flower bud formation according to claim 2 wherein said fatty acid is 12-oxo-13-hydroxy-9(Z),15(Z)-octadecadienoic acid.

5. The method for inducing flower bud formation according to claim 2 wherein said fatty acid is 10-oxo-13-hydroxy-11(E),15(Z)-octadecadienoic acid.

6. The method for inducing flower bud formation according to claim 2 wherein said fatty acid is 9-hydroxy-12-oxo-10(E),15(Z)-octadecadienoic acid.

7. A method for inducing flower bud formation comprising:
   applying to plants an agent for inducing flower bud formation comprising a fatty acid of 16 to 24 carbon atoms having an oxo group, a hydroxy group and a hydroperoxy group and containing 0 to 6 double bonds.

8. The method for inducing flower bud formation according to claim 7 wherein the oxo group and the hydroxy group in said fatty acid constitute an $\alpha$-ketol structure.

9. The method for inducing flower bud formation according to claim 8 wherein the number of carbon atoms in said fatty acid is 18.

10. The method for inducing flower bud formation according to claim 9 wherein said fatty acid is 9-hydroperoxy-12-oxo-13-hydroxy-10(E),15(Z)-octadecadienoic acid.

11. The method for inducing flower bud formation according to claim 9 wherein said fatty acid is 9-hydroxy-9-oxo-13-hydroperoxy-11(E),15(Z)-octadecadienoic acid.

12. An method for inducing flower bud formation comprising applying to plants an agent comprising a fatty acid of 16 to 24 carbon atoms having a hydroperoxy group and containing 0 to 6 double bonds.

13. The method for inducing flower bud formation according to claim 12 wherein the number of carbon atoms in said fatty acid is 18.

14. The method for inducing flower bud formation according to claim 13 wherein said fatty acid is 9-hydroperoxy-10(E),12(Z),15(Z)-octadecatrienoic acid.

15. The method for inducing flower bud formation according to claim 13 wherein said fatty acid is 13-hydroperoxy-9(Z),11(E),15(Z)-octadecatrienoic acid.

16. A method for inducing flower bud formation according to claim 1 wherein the agent further comprises norepinephrine.

17. A method for inducing flower bud formation according to claim 7 wherein the agent further comprises norepinephrine.

18. A method for inducing flower bud formation according to claim 12 wherein the agent further comprises norepinephrine.

* * * * *